US00PP30409P2

(12) United States Plant Patent
Korlipara

(10) Patent No.: US PP30,409 P2
(45) Date of Patent: Apr. 16, 2019

(54) ***ECHINACEA* PLANT NAMED 'TNECHPC'**

(50) Latin Name: ***Echinacea* spp.**
Varietal Denomination: TNECHPC

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/932,026

(22) Filed: Jan. 25, 2018

(51) Int. Cl.
*A01H 5/02* (2018.01)

(52) U.S. Cl.
USPC ..... Plt./428

(58) Field of Classification Search
USPC ..... Plt./428
See application file for complete search history.

*Primary Examiner* — Susan McCormick Ewoldt
(74) *Attorney, Agent, or Firm* — Klarquist Sparkman, LLP

(57) ABSTRACT

A new and distinct *Echinacea* plant named 'TNECHPC' is provided herein, characterized by medium size, red to red-orange ray florets, cinnamon-colored, anemone type, semi-double disc florets, an amazing number of inflorescences starting in the first season, a very compact habit, very long bloom time with excellent rebloom, and excellent vigor.

1 Drawing Sheet

Botanical denomination: *Echinacea* spp.
Variety designation: 'TNECHPC'.

BACKGROUND OF THE INVENTION

The present invention relates to a new and distinct cultivar of *Echinacea* and given the cultivar name 'TNECHPC'. *Echinacea* is in the family Asteraceae. The new cultivar is part of a planned breeding program for a landscape series with very compact habits and profuse inflorescences. The exact parents of this selection are unknown, unnamed, proprietary interspecific hybrids bred from *Echinacea paradoxa, Echinacea purpurea*, and *Echinacea tennesseensis.*

The trademark designation for the claimed plant is 'Prima™ Cinnamon'.

Compared to *Echinacea purpurea* 'Pas702917', Pow-Wow® Wild Berry, an unpatented plant, the new cultivar is of hybrid origin and has semi-double flowers rather than single, and flowers that are red orange rather than red purple. Both have small habits and flowers.

This new *Echinacea* cultivar is uniquely distinguished by:

1. medium size, red to red-orange ray florets,
2. cinnamon-colored, anemone type, semi-double disc florets,
3. an amazing number of inflorescences starting in the first season,
4. a very compact habit,
5. very long bloom time with excellent rebloom, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a two-year-old *Echinacea* 'TNECHPC' growing in the trial field in full sun in early September in Canby, Oreg.

DETAILED PLANT DESCRIPTION

The following is a detailed description of the new *Echinacea* cultivar based on observations of 8-month-old specimens growing in the trial field in full sun in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart,* 5$^{th}$ edition, 2007.

Plant:

*Type.*—Herbaceous perennial.
*Hardiness.*—USDA Zones 4 to 9.
*Size.*—Grows to 39 cm wide and 38 cm tall to top of inflorescences.
*Form.*—Basal clump, with 4 to 6 stems from the base.
*Vigor.*—Excellent.
*Roots.*—Fibrous, with many downward growing and few laterals, ivory in color, Yellow White 158D, roots develop easily from cuttings from the crown.

Leaf (stem):

*Type.*—Simple.
*Shape.*—Lanceolate.
*Arrangement.*—Alternate.
*Blade size.*—Grows to 9.5 cm long and 4 cm wide.
*Margins.*—Entire, slightly undulate.
*Apex.*—Acuminate.
*Base.*—Attenuate.

*Surface texture*.—Strigose on both sides.

*Venation*.—Pinnate, Yellow Green 145C on both sides.

*Color*.—Topside Green N137B, bottom side closest to Yellow Green 147B.

*Petiole description*.—Clasping, grows to 5 cm long and 7 mm wide, pubescent, narrow leafy edges which fold upwards, Yellow Green 146C.

Inflorescence:

*Type*.—Composite on terminal stalked heads.

*Flowering stem*.—Grows to 33 cm tall from the base of the plant to the terminal inflorescence and can grow to 10 cm long from the top stem leaf to the base of an inflorescence; unbranched to branched, with 1 to 11 inflorescences per stem; diameter growing to 6 mm wide near the inflorescence; strigose; Yellow Green 145B strongly tinted Greyed Purple 187B.

*Size*.—Grows to 6.5 cm wide and 4.5 cm deep as disc enlarges.

*Form*.—Ray florets held horizontally, curving down in old inflorescences, mature disc is conic.

*Immature inflorescence* (*bud*).—4 cm wide and 2 cm deep, ray florets held at 30 degree angle and rolled up so only the back color shows, Greyed Purple 185B, disc color Greyed Purple 187B.

*Ray florets*.—Without pistil or stamen, 19 to 27 in number, grow to 28 mm long and 11 mm wide, oblanceolate with the tip three-toothed, cut ⅔, tips acute to obtuse, entire margins, base cuneate, glabrous on both sides; fully open florets topside Red 46A, bottom side Greyed Purple 185B; florets fade gradually to topside Greyed Orange 165B at top half blending to Red 46A at base, bottom side Greyed Orange 177D, tinted Greyed Purple 187C in bottom ⅔.

*Disc*.—Flat becoming conic, becoming 30 mm deep and 40 mm wide with maturity, Greyed Purple 185A.

*Disc florets*.—About 260 in number, each with 1 pistil and 4 stamen, grow to 14 mm long and 5 mm wide, each with one persistent, very stiff linear bract (12 mm long with the top 2 mm Greyed Purple 187B blending to 2 mm Orange 23B to 4 mm Green 137A blending to White NN155A on bottom); corolla 11 mm long and 5 mm wide, tubular, 5 lobed, glabrous inside and out, outside Greyed Purple 185A on top half and blending to Yellow Green 152B on bottom, inside Red Purple 60A with tips Greyed Purple 187A; pistil 10 mm long, ovary 4.5 mm long, White NN155D with top Yellow Green 144A, style 4.5 mm long White NN155A, 2-branched stigma spreading 2 mm wide, Greyed Purple 187B to 187A on tips; stamen 4 mm long, filaments 2 mm long and White NN155B, anthers 3 mm long and Brown N200A, pollen none.

*Involucral bracts*.—In 4 leafy series, area grows to 38 mm wide and 10 mm deep, lobes lanceolate in shape, reflexed, grow to 10 mm long and 5 mm wide, Green N137A, margins strigose, tip acute, strigose on both sides.

*Receptacle*.—Grows to 17 mm wide and 25 mm deep, White NN155B.

*Bloom period*.—June through October in Canby, Oreg.

*Fragrance*.—Slight.

*Lastingness*.—Each inflorescence lasts about two weeks in Canby, Oreg.

Seeds: None.

*Fertility*.—None.

Disease and pests: No pests or diseases have been observed on plants grown under commercial conditions in Canby, Oreg. No resistances are known.

I claim:

1. A new and distinct *Echinacea* plant as herein illustrated and described.

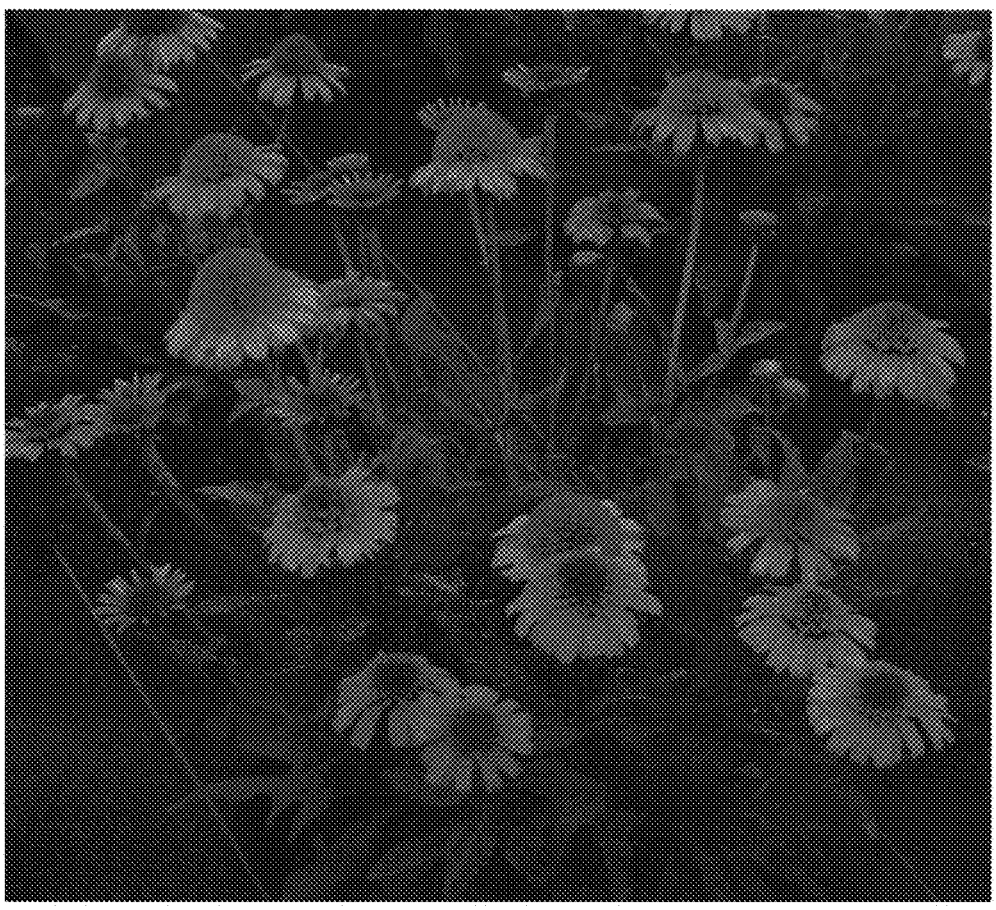

* * * * *